United States Patent [19]

Fujiwara et al.

[11] Patent Number: 5,258,550

[45] Date of Patent: Nov. 2, 1993

[54] PROCESS FOR PREPARING GLYCINE

[75] Inventors: Kenji Fujiwara; Nobutaka Ueda; Yuuji Matsuu; Hiroshi Kato; Atsuhiko Hiai, all of Takaishi, Japan

[73] Assignee: Mitsui Toatsu Chemicals, Incorporated, Tokyo, Japan

[21] Appl. No.: 720,825

[22] PCT Filed: Dec. 5, 1990

[86] PCT No.: PCT/JP90/01576

§ 371 Date: Jul. 8, 1991

§ 102(e) Date: Jul. 8, 1991

[87] PCT Pub. No.: WO91/08194

PCT Pub. Date: Jun. 13, 1991

[30] Foreign Application Priority Data

Dec. 6, 1989 [JP] Japan .................. 1-315139

[51] Int. Cl.$^5$ ............................ C07C 229/00
[52] U.S. Cl. .................................... 562/575
[58] Field of Search .......................... 562/575

[56] References Cited

U.S. PATENT DOCUMENTS 3,536,726 10/1970 Fink et al. .

5,202,479 4/1993 Fujiwara ..................... 562/575

FOREIGN PATENT DOCUMENTS 53-28115 3/1978 Japan .
53-28116 3/1978 Japan .
53-31616 3/1978 Japan .
2-108653 4/1990 Japan .
2-157252 6/1990 Japan .

Primary Examiner—Michael L. Shippen
Attorney, Agent, or Firm—Burns, Doane, Swecker & Mathis

[57] ABSTRACT

This invention relate to a process for producing glycine by reacting glycolonitrile, carbon dioxide and ammonia in the presence of water, comprising subjecting first water, glycolonitrile, carbon dioxide and ammonia to a pre-reaction at 80°–120° C. for 0.5–1 hour and then to the main reaction at 150°–200° C. and a process further comprising recycling the remaining mother liquor having separated the glycine from the reaction solution obtained by the above process to the system comprising water, glycolonitrile, carbon dioxide and ammonia to carry out the aforesaid pre-reaction and/or main reaction.

6 Claims, No Drawings

PROCESS FOR PREPARING GLYCINE

TECHNICAL FIELD

This invention relates to a process for preparing glycine. More particularly, the invention relates to a process for preparing glycine by reacting glycolonitrile with ammonia and carbon dioxide.

BACKGROUND ART

Glycine is a valuable compound of wide use as food additives for processed foodstuffs and raw materials for agricultural chemicals and medicines.

Among conventionally known preparation processes of glycine are predominantly the amination process of monochloroacetic acid, the Strecker process, the hydantoin process, etc. Although the monochloroacetic acid process is advantageous in that it does not employ toxic hydrogen cyanide, it byproduces secondary and tertiary amine homologues, resulting in low glycine yields. Further, in the Strecker process, it is necessary to separate iminodiacetic acid salts byproduced upon the reaction or neutralized salts after hydrolysis.

The hydantoin process produces glycine by the hydrolysis of hydantoin obtained from hydrogen cyanide and formaldehyde used as starting materials. For example, hydrogen cyanide, the aldehyde, ammonia and carbon dioxide are heated at not lower than 100° C. in aqueous solvents (U.S. Pat. No. 3,536,726). In other approaches of the process, hydrogen cyanide, formaldehyde and ammonium carbonate are heated in an aqueous medium, or glycolonitrile, ammonia and carbon dioxide are reacted by heating followed by the removal of unreacted ammonia and carbon dioxide and the subsequent treatment with an alkylamine or alkyl ammonium hydroxide. In further approaches, glycolonitrile, ammonia and carbon dioxide are reacted by heating followed by the removal of unreacted ammonia and carbon dioxide and the subsequent treatment with a mineral acid for hydrolysis, or glycolonitrile, ammonia and carbon dioxide are reacted by heating followed by the treatment with an alkaline material such as the hydroxides, carbonates and bicarbonates of alkali metals or alkaline earth metals.

However, all of these processes produce byproducts in considerable amounts so that their glycine selectivities can not be said satisfactory. In the process in which hydantoins are hydrolyzed by a alkali salt or metal, the selectivity of glycine is improved, but the alkali is needed in molar equivalent or more to the glycolonitrile charged and moreover the glycine salt needs to be hydrolyzed. Further, the complicated separation step of glycine from byproduced salts, such as sodium sulfate and sodium chloride, not only deteriorates greatly the economical efficiency of the glycine production but also raises problems in treating the salts. In the industrial execution of the process, glycine must be isolated from the solution as crystals, in which case the glycine yield is inevitably lower than the one-pass glycine yield.

The foregoing U.S. Pat. No. 3,536,726 discloses a process in which glycine is produced via hydantoin without formation of such byproduced salts and most of the glycine is crystallized out from the reaction solution, the residual solution from which the crystallized glycine has been separated (referred simply to as the mother liquor hereunder) being recycled to the reaction zone (hereinafter simply referred to as the mother liquor recycle process). However, further improvement in the yield of glycine and reduction in the amount of byproducts are desired.

The present inventors have made intensive investigations into a process whereby glycine yield is improved in the production of glycine based on the hydantoin process. As a result, it has been found that by first subjecting glycolonitrile to a pre-reaction at a lower temperature than the main reaction temperature to convert it to another compound which is more stable than glycolonitrile and subsequently subjecting the compound to the main reaction at the predetermined higher temperature, the yields of glycine and products convertible to glycine are greatly improved. The present invention has been completed on the basis of this discovery.

DISCLOSURE OF THE INVENTION

According to the present invention, there is provided the aforesaid process for preparing glycine by reacting glycolonitrile, carbon dioxide and ammonia in the presence of water, which process comprises first subjecting water, glycolonitrile, carbon dioxide and ammonia to a pre-reaction at 80°-120° C. for 0.5-1 hour and then subjecting the resulting reaction system to the main reaction at 150°-200° C.

The most preferred embodiment of the present invention is such that glycine is separatead by a separation means including crystallization from the reaction solution containing the glycine and the remaining mother liquor from which the glycine has been separatead is recycled to the system comprising water, glycolonitrile, carbon dioxide and ammonia, which is then subjected to the pre-reaction and the main reaction. This process is referred to as the mother liquor recycle process hereunder.

It is important in the present invention to subject glycolonitrile along with carbon dioxide and ammonia to a pre-reaction at a lower temperature than the glycine formation reaction temperature, i.e., at 80°-120° C. in the presence of water, in the prior stage to the glycine formation reaction. In this way, the glycolonitrile is converted to a more stable compound. Since this procedure may also produce byproducts convertible to glycine as described below, it can be expected that the incorporation of the pre-reaction and the mother liquor recycle process may further improve the yield of glycine isolation.

The glycolonitrile used in the present invention is prepared using hydrocyanic acid and formaline as raw materials. This process is the most common and economical preparation process of glycolonitrile. As the formaline source, paraformaldehyde may be used by dissolving it in water. However, since there is no particular limitation on the concentration of glycolonitrile in the production of glycine, it is most economical and simple to use approx. 37 wt. % formaline as the formaline. Since the reaction proceeds quantitatively, the concentration of the glycolonitrile thus obtained reaches about 50 wt. %, and it is quite reasonable and economical to use the 50 wt. % aqueous glycolonitrile solution as it is as a starting material for the production of glycine. Further, the aqueous glycolonitrile solution used in the process of the present invention may contain sulfuric acid or phosphoric acid, which is useful as a stabilizing agent of glycolonitrile, without any obstacle.

The aqueous glycolonitrile solution is preferably stored at low temperatures in view of preventing its polymerization, decomposition or the accompanying coloring until it comes in contact with carbon dioxide and ammonia. The solution stored at 40° C. or below will make no trouble for practical use.

The ammonia and carbon dioxide used in the process of the present invention may be used as they are. It is however possible to use compounds which form these compounds (ammonia and carbon dioxide) under the reaction conditions and are known to persons skilled in the art, such as ammonium carbonate and ammonium bicarbonate. Further, the use of a mixture of these compounds may also give favorable results.

The amount of ammonia to be used is in the range of 2-12 moles, preferably 4-9 moles, per mole of the sum of glycolonitrile. If the amount of ammonia is less than 2 moles, the reaction will be retarded, whereas any amounts in excess of 12 moles will unfavorably increase the amount of byproducts and raise the reaction pressure, though accelerate the reaction.

The sum of glycolonitrile means the total of the glycolonitrile freshly fed to the reactor plus the byproducts convertible to glycine described below which are contained in the recycle mother liquor in the mother liquor recycle process, the byproducts being expressed in terms of glycolonitrile.

The amount of carbon dioxide to be used is ⅛-1 mole per mole of ammonia, approx. ¼ mole being preferably employed in view of the reaction rate and reaction pressure.

The amount of water to be used is 5-15 moles per mole of ammonia. If the amount of water is less than 5 moles, the selectivity of glycine will be worsened and the crystallization ratio of glycine will be extremely reduced. On the other hand, any amount in excess of 15 moles will decrease the concentration of glycine in the reaction solution, though it improves the selectivity of glycine, thus not only increasing the concentration cost for crystallization but also adding to the volume of the reactor. Therefore, any amounts outside the range are not economical. Further, when a higher reaction temperature is employed, it is preferable to use this molar ratio of a higher level.

No particular restrictions are imposed on the reaction pressure. Therefore, the reaction may be effected under a higher pressure than that developed during the reaction or under a controlled pressure by proper extraction of gases such as ammonia, carbon dioxide, solvent vapors evolved in the course of the reaction.

The lower the reaction temperature in the process of the present invention, the more improved is the yield of glycine, but the reaction rate will be reduced. Accordingly, the reaction temperature is 150°-200° C., preferably 150°-180° C., more preferably 150°-170° C.

The reaction solution obtained according to the process of the present invention contains glycine and byproducts such as hydantoic acid, glycylclycine, hydantoic acid amide, triglycine, hydantoin and 2,5-diketopiperazine. First, glycine is separated from the reaction solution containing these byproducts by, for example, the crystallization process as described below. The present inventors have found that glycine yield is significantly improved by recycling these byproducts contained in the mother liquor after separating the glycine to the reactor where the reactions (to be exact, pre-reaction and/or main reaction) are carried out in the system comprising water, glycolonitrile, carbon dioxide and ammonia. This may be ascribable to the novel finding of the present inventors that the byproducts and the glycine are present in equilibrium during the reaction, and when the aforesaid mother liquor is recycled to the reactor where the reactions are conducted (hereinafter simply referred to as the reactor), the equilibrium moves to the glycine side from the byproduct side by the amount of the glycine separated/removed by the crystallization process. In consequence, the present inventors have found that by recycling the mother liquor to the reactor (particularly to the region where the main reaction is being carried out), the yield of the glycine isolated as crystals based on the glycolonitrile (isolated yield : one in the stream is generally referred to as "the yield", while the yield of the isolated product as "the isolated yield") is improved to 75% or higher. Where the mother liquor is not recycled, the isolated yield of the glycine practically separated as crystals is at most about 60%, even if the one-pass glycine yield is high. Hence, at least, the above-described byproducts can be considered convertible to glycine under the reaction conditions prescribed in the present invention. In the process in which the mother liquor is recycled to the reactor, the one-pass yield of glycine is added with the amount converted to glycine of the aforesaid convertible byproducts in the mother liquor so that the yield of the glycine isolated, i.e. the isolated yield is improved.

The compositions of glycine and byproducts convertible to glycine during the reaction are determined by the reaction temperature, the concentrations of ammonia, carbon dioxide, water and glycolonitrile and the reaction time. An excessively long pre-reaction time leads to an unduly long total average residence time, which is the sum of the average residence time at the pre-reaction temperature and at the main reaction temperature of glycine formation, and hence is uneconomical. When the time for the pre-reaction is too short, its effect will be extremely small. A preferred pre-reaction time is 0.5-1 hour. Further, when the pre-reaction temperature is lower than 80° C., glycolonitrile is converted to colored substances by side reactions in increased amounts, so that the yields of glycine and byproducts convertible to glycine are reduced. If the pre-reaction temperature is considerably higher than 120° C., the effect of the pre-reaction may not be exhibited. The pre-reaction temperature may more preferably be in the range of 100°-120° C. The pre-reaction may be carried out by providing another preliminary reactor prior to the main reactor of glycine formation, or by providing a certain section (region) for the pre-reaction controlled at 80°-120° C. in the former part of a longitudinally long tubular reactor in accordance with each residence time.

It is more preferable to pre-heat water, carbon dioxide, ammonia and glycolonitrile to 80°-120° C. in advance and feed them to carry out the pre-reaction at the same temperature.

The starting glycolonitrile may preferably be fed so as to attain a fixed value in the sum of its amount and the amount, in terms of glycolonitrile, of the byproducts convertible to glycine in the mother liquor recycled to the reactor.

The reaction solution obtained in the process of the present invention is concentrated at 50°-120° C. to separate/remove most of the water and the ammonia and carbon dioxide from the reaction mixture.

Then, the reaction mixture is allowed to cool to 5°-80° C. to obtain a mother liquor containing glycine crystals.

The process for crystallizing glycine from the reaction mixture is carried out in the manner known to those skilled in the art, and it does not limit the process of the present invention. For example, crystallization processes such as the cooling-, evaporation- and vacuum-crystallization processes may preferably be employed industrially.

The mother liquor containing glycine crystals obtained by the crystallization undergoes solid-liquid separation by means of a conventional separator, whereby 50% or more of the glycine is generally isolated. On the other hand, all or part of the mother liquor obtained is fed back to the reaction step. Favorable results may also be obtained by recycling all of the mother liquor which has optionally undergone a decoloring process or by recycling the same mother liquor from which its portion is discarded.

The amount of glycine and byproducts such as glycylglycine, triglycine, hydantoin, hydantoic acid, hydantoic acid amide, 2,5-diketopiperazine, in the mother liquor recycled according to the process of the present invention varies depending on the crystallization rate determined by the amounts of glycine and the byproducts in the reaction solution and the intended purity of glycine. Namely, when the crystallization ratio of glycine is reduced for the purpose of producing glycine of a high purity, the amount of the mother liquor recycling is increased and hence the energy for the concentration/crystallization is unfavorably made larger. On the contrary, if the crystallization ratio is increased with a view to reducing the recycling amount, the purity of the glycine obtained is generally reduced. Therefore, the converted glycolonitrile amount in the mother liquor is commonly not less than 30% by mole and not more than 200% by mole based on the freshly charged glycolonitrile.

The process of the present invention may be effected in the manner of batch, semi-batch or flow process.

EXAMPLES

The process of the present invention will be described specifically with reference to the following examples.

EXAMPLE 1

A mixture of 230 g (2.01 moles) of a 50 wt. % aqueous glycolonitrile solution of 25° C. and 1990 g of an aqueous solution containing 206 g (12.1 moles) of ammonia and 267 g (6.1 moles) of carbon dioxide and preheated to 100° C. was fed, per hour, into a tubular reactor having an inner volume of 10 liters at its bottom. The reactions were conducted in such a way that the 1/5-portion of the reactor from the inlet was controlled at 100° C. and the rest 4/5-portion at 150° C. The reaction pressure employed was 50 kg/cm$^2$. The composition of the starting materials in molar ratio was $H_2O:NH_3:CO_2$:glycolonitrile=45:6:3:1. The average residence time at 100° C. was 1 hour and that at 150° C. was 4 hours, corresponding to 5 hours in total.

After the reactions had become steady, the reaction solution was concentrated in a concentrator to remove water, ammonia and carbon dioxide, thereby undergoing crystallization (crystallization ratio: 55%) to separate 0.890 mole of glycine (purity: 98.2%) per hour. The analysis of the remaining mother liquor detected the presence of 0.97 mole of hydantoic acid, glycylglycine, hydantoic acid amide, 2,5-diketopiperazine, hydantoin, triglycine and glycine in terms of glycolonitrile. Thus, the mother liquor to be used for initial charge was prepared. In the above operations, the yield of glycine and the yield of glycine plus the byproducts detected as described above based on glycolonitrile are shown in Table 1 as one-pass glycine yield and H-GLY (hypothetical glycine yield), respectively. Subsequently, the mother liquor, 50 wt. % aqueous glycolonitrile solution and aqueous ammonium carbonate solution were fed to the reactor in such a way that the same composition of the starting materials (in molar ratio) as described above was attained by assuming the glycolonitrile as the total of glycolonitrile and glycolonitrile equivalent of the byproducts. Specifically, the mother liquor, 118 g (1.04 mole) of a 50 wt. % aqueous glycolonitrile solution and an aqueous solution containing 6.1 moles of ammonium carbonate were fed to the reactor. After establishment of the steady state, the reactions were carried out for 24 hours. As a result, 1.64 kg of isolated glycine was obtained (crystallization ratio: 55%). This corresponds to a yield (glycine isolated yield) of 88.2% based on the charged glycolonitrile. The results are shown in Table 1.

On the other hand, upon reaching the steady state, a portion of the reaction solution was sampled separately and concentrated further to crystal out a larger amount of glycine. In consequence, glycine of 98.0% purity could be isolated at a crystallization ratio of 66%. This means that the crystallization ratio can be increased from 55% to as high as 66% in the procedure of Example 1. By employing this condition, it is possible to further decrease the amount of the mother liquor recycling.

COMPARATIVE EXAMPLE 1

The procedure of Example 1 was followed except that the aqueous glycolonitrile solution and the aqueous ammonium carbonate solution were mixed together at 25° C. and the same total residence time was adopted in the absence of the pre-reaction. The results are given in Table 1.

COMPARATIVE EXAMPLE 2

The procedure of Example 1 was followed except that the aqueous ammonium carbonate solution having been preheated to the reaction temperature of 150° C. was mixed with the aqueous glycolonitrile solution without the pre-reaction. The results are shown in Table 1.

In this comparative example, a portion of the reaction solution under the steady state was sampled separately and concentrated further with the intention of crystallizing out a greater amount of glycine. In the course of the concentration, however, the viscosity of the reaction solution increased abruptly to form a tarry material, thus making it entirely impossible to carry out the crystallization operation. This may presumably be attributable to accumulation of impurities (byproducts) obstructing the crystallization operation in as large an amount as correspond to the decrease of the glycine yield in the case of this comparative example. The present inventors have confirmed that if the amount of the by-products is small in the reaction solution, any further concentration of the solution will not produce a tarry material so that the crystallization operation is always possible.

EXAMPLE 2

The procedure of Example 1 was followed except that the aqueous ammonium carbonate solution preheated to 120° C. was mixed with the aqueous glycolonitrile solution, the pre-reaction was carried out at 120° C. for 0.5 hour, and the main reaction was so effected that the total residence time was the same. The results are shown in Table 1.

ence on the crystallization operation and hence causes large variation in the crystallization ratio of glycine.

According to the process of the present invention, it is possible not only to improve the yield, but also to lessen the accumulation of impurities as described above. Therefore, the process has a marked feature in that an increased ratio of concentration to a considerably high degree will not interfere with the crystallization operation.

TABLE 1

| Example | Preheating Temperature of Aqueous Ammonium Carbonate (°C.) | Pre-Reaction Temperature (°C.) | Pre-Reaction Time (hr) | Main Reaction Temperature (°C.) | Main Reaction Time (hr) | Total Residence Time (hr) | One Pass Yield Glycine | One Pass Yield H—GLY | Glycine Isolated Yield (%) |
|---|---|---|---|---|---|---|---|---|---|
| Example 1 | 100 | 100 | 1.0 | 150 | 4.0 | 5.0 | 79.6 | 93.8 | 88.2 |
| Comp. Ex. 1 | 25 | — | — | 150 | 5.0 | 5.0 | 70.3 | 82.7 | 78.1 |
| Comp. Ex. 2 | 150 | — | — | 150 | 5.0 | 5.0 | 76.4 | 88.9 | 82.5 |
| Example 2 | 120 | 120 | 0.5 | 150 | 4.5 | 5.0 | 79.9 | 92.9 | 88.1 |
| Example 3 | 100 | 100 | 0.5 | 170 | 2.0 | 2.5 | 65.4 | 89.2 | 83.2 |
| Example 4 | 120 | 120 | 0.5 | 170 | 2.0 | 2.5 | 65.6 | 90.3 | 82.9 |
| Comp. Ex. 3 | 170 | — | — | 170 | 2.5 | 2.5 | 62.1 | 85.0 | 77.9 |

H—GLY: Yield of Components = glycine + hydantoic acid + glycylglycine + hydantoin + hydantoic acid amide + triglycine + 2,5-diketopiperazine based on glycolonitrile (%)

EXAMPLE 3

The same procedure as described in Example 1 was followed except that the composition of the starting materials in molar ratio was $H_2O:NH_3:CO_2:$glycolonitrile$=45:5:2.5:1$, the reaction time of the prereaction was 0.5 hour, and the reaction temperature and reaction time of the main reaction were 170° C. and 2 hours, respectively. The results are shown in Table 1.

Further, part of the reaction solution was concentrated separately in the same manner as in Example 1 to obtain a highly concentrated solution. As a result, glycine could be separated with a purity of 97.8% at a crystallization ratio of 62%.

EXAMPLE 4

The same procedure as in Example 3 was followed except that the preheating temperature of the aqueous ammonium carbonate solution and the reaction temperature of the pre-reaction were both changed to 120° C. The results are shown in Table 1.

COMPARATIVE EXAMPLE 3

The same procedure as in Example 3 was followed except that the aqueous ammonium carbonate solution having been preheated to the reaction temperature of 170° C. was mixed with the aqueous glycolonitrile solution without the pre-reaction. The results are given in Table 1.

Further, in the same manner as in Example 3, an attempt was made to concentrate a portion of the reaction solution having been sampled separately. Then, in the course of the concentration, the reaction solution turned tarry as in Comparative Example 2, so that the crystallization operation was quite impossible to perform. Namely, this comparative example have clarified the presence of such a serious problem that an increased concentration ratio immediately causes the crystallization to be inoperable.

As described above, the accumulation of impurities upon the formation of glycine exerts significant influ-

APPLICABILITY IN INDUSTRY

In the present invention, a pre-reaction of the starting materials in the course of the production of glycine gives the stable compound and also materials convertible to glycine in high yields. In consequence, the yield of glycine (particularly, glycine obtained practically as crystals) is drastically improved. Further, the application of the process to the mother liquor recycle process which produces no waste liquor has improved the yield of glycine to a further large extent and hence enhanced the production of glycine via hydantoin to an industrially practicable process.

We claim:

1. A process for producing glycine by reacting glycolonitrile, carbon dioxide and ammonia in the presence of water, which process comprises subjecting water, glycolonitrile, carbon dioxide and ammonia to a pre-reaction at 80°–120° C. for 0.5–1 hour and then to the main reaction at 150°–200° C.

2. A process according to claim 1 wherein the glycine is obtained as a reaction solution containing the same.

3. A process according to claim 2 which further comprises the step of separating the glycine from the reaction solution.

4. A process according to claim 3 wherein the separation of the glycine from the reaction solution is effected by crystallization.

5. A process according to claim 1 wherein the remaining mother liquor having separated the glycine from the reaction solution is recycled to the system comprising water, glycolonitrile, carbon dioxide and ammonia to perform the pre-reaction and/or the main reaction.

6. A process according to claim 1 wherein the glycolonitrile is introduced into the water, carbon dioxide and ammonia preheated in advance to 80°–120° C. to perform the pre-reaction at the same temperature for 0.5–1 hour.

* * * * *